United States Patent
Okuda et al.

(10) Patent No.: US 7,538,201 B2
(45) Date of Patent: May 26, 2009

(54) RECOMBINANT HERPESVIRUS AND USES THEREOF

(75) Inventors: Takashi Okuda, Tokyo (JP); Shuji Saitoh, Tokyo (JP); Sakiko Saeki, Tokyo (JP)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 10/594,449

(22) PCT Filed: Mar. 9, 2005

(86) PCT No.: PCT/JP2005/004585

§ 371 (c)(1),
(2), (4) Date: Sep. 26, 2006

(87) PCT Pub. No.: WO2005/093070

PCT Pub. Date: Oct. 6, 2005

(65) Prior Publication Data

US 2007/0212377 A1    Sep. 13, 2007

(30) Foreign Application Priority Data

Mar. 29, 2004    (JP)    ............................ 2004-095500

(51) Int. Cl.
*C07H 21/04*    (2006.01)
*C12N 7/00*    (2006.01)

(52) U.S. Cl. .................................. 536/23.1; 435/235.1

(58) Field of Classification Search ........................ None
See application file for complete search history.

(56) References Cited

U.S. PATENT DOCUMENTS

| 5,443,831 | A |   | 8/1995  | Keeler et al.         |
|-----------|---|---|---------|-----------------------|
| 5,980,906 | A | * | 11/1999 | Audonnet et al. ........ 424/199.1 |
| 6,001,369 | A |   | 12/1999 | Cochran et al. .......... 424/229.1 |
| 6,183,753 | B1| * | 2/2001  | Cochran et al. .......... 424/199.1 |
| 6,632,664 | B1|   | 10/2003 | Saitoh et al.         |

FOREIGN PATENT DOCUMENTS

| JP | 11-192093   |   | 7/1999   |
|----|-------------|---|----------|
| JP | 2001-188    |   | 1/2001   |
| WO | WO 93/25665 | * | 12/1993  |

OTHER PUBLICATIONS

Tong et al., Protection of chickens from infectious laryngotracheitis with a recombinant fowlpox virus expressing glycoprotein B of infectious laryngotracheitis virus, Avian Pathology, 2001, 30:142-148.*

European Search Report dated Feb. 27, 2007.

* cited by examiner

*Primary Examiner*—Bruce Campell
*Assistant Examiner*—Nicole Kinsey White
(74) *Attorney, Agent, or Firm*—Kratz, Quintos & Hanson, LLP (57) ABSTRACT

A recombinant herpesvirus (excluding infectious laryngotracheitis virus) having a DNA that encodes a polypeptide comprising 429 amino acids at the amino terminal end of a protein encoded by the gB gene of infectious laryngotracheitis virus or a polypeptide in which one or a plurality of amino acids have been deleted, added, or substituted in said polypeptide.

12 Claims, 2 Drawing Sheets

RECOMBINANT HERPESVIRUS AND USES THEREOF

TECHNICAL FIELD

The present invention relates to a recombinant herpesvirus having DNA that encodes the gB gene of infectious laryngotracheitis virus (hereinafter referred to as ILTV), and uses thereof. More specifically, it relates to a recombinant herpesvirus having a partial sequence of the gB gene of ILTV that can be stably present in the recombinant, and a vaccine against infectious laryngotracheitis virus.

BACKGROUND ART

Infectious laryngotracheitis is caused by the infection of ILTV. ILTV infects avians such as chickens, pheasants, peacocks and turkeys. Characteristic features of onset in chickens include the appearance of respiratory symptoms, elevation of body temperature and anorexia and the like, serious coughing, expectoration of sputums. When egg-laying chickens are infected, the rate of laying eggs starts to decrease about four days after the onset of the disease, and takes about one month before normal egg-laying returns. Furthermore, increases in death rate due to mixed infection of ILTV and other pathogens have been reported, and infectious laryngotracheitis inflicts huge economic losses on the poultry industry.

For the prevention of infectious laryngotracheitis, dried live vaccines or frozen live vaccines from attenuated vaccine strains have conventionally been used. However, the effect of immunization varies with the breeding environment, the breeding density, the inoculation method and the like. Furthermore, there are also risks that vaccination may cause slight symptoms in the respiratory tract and faulty methods or amounts of inoculation may lead to the onset of the disease. In some areas, there are reports of diseases caused by the reverted pathogenicity of vaccine strains, and thus the development of safe and effective vaccines is being sought.

In order to overcome the problems, recently, vaccines comprising as an active ingredient a recombinant virus vector have been developed by the recombinant technology. With regard to ILTV, the use of fowlpox virus (hereinafter referred to as FPV) as the virus vector has been investigated and it is commercially available in the USA (BIOMUNE, trade name VECTORMUNE FP-LT(+AE)).

ILTV is a causative virus of infectious laryngotracheitis. ILTV is one of the herpesviruses and the virus genome consists of a double stranded DNA comprising about 160,000 base pairs. There are known the thymidine kinase gene (Griffin et al., J. Gen. Virol. 71:841, 1990), gp60 gene (Kongsuwan et al., Virus Genes 7:297-303, 1993), the capsid p40 gene (Griffin et al., Nucleic Acids Res. 18:366, 1990), the glycoprotein B (gB) gene (Poulsen et al., Virus Genes 5:335-347, 1991; Griffin et al., J. Gen. Virol. 72:393-398, 1991; U.S. Pat. No. 5,443,831), the glycoprotein C (gC) gene (Kingsley et al., Virology 203:336-343, 1994), the RR2 gene (Griffin et al., J. of General Virol. 70:3085-3089, 1989), the UL32 gene (International Patent Publication WO98/07866), and the like.

The open reading frame of gB gene of ILTV has a full-length of 2613 bp (873 amino acids), and it is reported in U.S. Pat. No. 5,443,831 etc. that a recombinant FPV having the full-length gene integrated therein exhibits an effect as a vaccine.

Poxviruses such as FPV rapidly grow in the host and after expressing the antigen protein, they are completely expelled from the host's immune system. However, as immunity is memorized and boosted after expelling the virus, the poxvirus is suitable for use as the host for vaccine. On the other hand, herpesviruses such as turkey herpesvirus (hereinafter referred to as HVT) do not rapidly grow in the host, and latent infection lasts for a long time. During this latency, herpesviruses continue to stimulate the immune system of the host. The use of recombinant HVT as a virus vector using such a characteristic is being investigated.

Although PCT Japanese National Publication No. 4-501658 (EP 434721) described that a recombinant HVT comprising HVT, into which an ILTV antigen gene has been inserted, has been constructed in fact the recombinant HVT has not been constructed.

In addition, in Japanese Unexamined Patent Publication No. 2001-000188, a recombinant HVT, into which two genes, i.e., a full-length gB gene of ILTV and an UL32 gene have been inserted, has been constructed. It has been confirmed that this recombinant HVT expresses in vitro a protein corresponding to the inserted gene using a immunofluorescent assay method, but an effect as a vaccine has not been confirmed.

DISCLOSURE OF THE INVENTION

Under the circumstances of the conventional technology, the present inventors have attempted to purify, by subculturing, a recombinant herpesvirus wherein a DNA molecule, in which a promoter was ligated upstream to the full-length gB gene of ILTV, has been inserted into the herpesvirus genome. However, the purification was impossible because of the deletion of ILTV gB gene. When the deletion of the gB gene occurs, the recombinant herpesvirus does not function as an anti-ILTV vaccine. Furthermore, ILTV and HVT are both herpesviruses, and HVT per se has the gB gene as an essential gene.

Thus, as gB genes may compete with each other at the time of forming virus particles, the present inventors thought that it would be important to avoid completion and to retain antigenicity by deleting the membrane anchor portion and the cytoplasmic domain of the gB gene product of ILTV so as to change the gB protein of ILTV from a membrane protein to a secretary protein.

Based on this idea, after intensive and extensive study in order to obtain recombinant herpesviruses that are stable during subculturing, the present inventors have found that a vaccine effect can be obtained by shortening the gB gene to a predetermined length in addition to deleting the membrane anchor portion and the cytoplasmic domain, and a higher vaccine effect can be obtained by ligating the shortened gB gene to a specific additive sequence, and therefore have completed the present invention.

Thus, in accordance with the present invention, there is provided a recombinant herpesvirus (excluding infectious laryngotracheitis virus) having a DNA that encodes a polypeptide comprising 429 amino acids at the amino terminal end of a protein encoded by the gB gene of infectious laryngotracheitis virus or a polypeptide in which one or a plurality of amino acids have been deleted, added, or substituted in said polypeptide. Furthermore, there is provided a vaccine against infectious laryngotracheitis virus comprising as an active ingredient said recombinant herpesvirus.

BEST MODE FOR CARRYING OUT THE INVENTION

The present invention will now be explained in detail hereinbelow.

DNA

DNA for use in the present invention is one (hereinafter referred to as the partial gB gene) that encodes a partial peptide comprising 429 amino acids at the amino terminal end of a protein (hereinafter referred to as the gB protein) encoded by the gB gene of ILTV. The amino acid sequence of this partial peptide may include the deletion, addition or substitution of one or a plurality of amino acids.

As a specific example of DNA for use in the present invention, there can be mentioned a DNA that encodes a sequence of 429 amino acids set forth in SEQ ID NO: 2, and as a specific example, there can be mentioned a DNA of a nucleotide sequence set forth in SEQ ID NO: 3.

As ILTV that can be an origin of the gB gene, there can be mentioned, for example, the NS-175 strain (the strain number VA0204 of the Catalog of Cultures for Animal Hygene, the Japanese Association of Veterinary Biologics), the CE strain (Kouda, Azabu Veterinary College Research Report, 31, 133-202, 1976), the SA-2 strain (Johnson et al., Arch. Virol., 119, 181-198, 1991), the highly toxic field isolate 632 strain (Keeler et al., Avian Diseases, 35, 920-929, 1991), and the USDA challenge strain (Poulsen et al., J. General. Virol., 78, 2945-2951, 1997).

The gB gene is not specifically limited, and any gene encoding the gB protein derived from ILTV may be used, and there can be mentioned, for example, the gB gene (GeneBank ACC. No. X56093) derived from the highly toxic field isolate 632 strain and the gB gene (GeneBank ACC. No. M64927) derived from the SA2 strain.

The vaccine effect can be enhanced by ligating a DNA (hereinafter referred to as the additive DNA) that encodes the amino acid sequence set forth in SEQ ID NO: 4 in frame with the 3'-end of the above-mentioned gB gene. One or a plurality of amino acids of the amino acid sequence set forth in SEQ ID NO: 4 may be deleted, added or substituted.

The linking of the additive DNA in a frame with the partial gB gene is both important and preferred in order to enhance the vaccine effect.

The amino acid sequence set forth in SEQ ID NO: 4 neither has a sequence that has some function nor has a sequence that is estimated to have some function. Among the nucleic acid sequence 120 bp (not containing the stop codon) (SEQ ID NO: 5) encoding the amino acid sequence set forth in SEQ ID NO: 4, 87 bp is derived from the SV40 polyadenylation signal, 16 bp from the UL45 of HVT, 13 bp from the artificially introduced SfiI sequence, and 4 bp is from the flanking sequence.

The method of ligating the partial gB gene and the additive DNA in a frame is not specifically limited, and a general method described in a textbook (Sambrook, J., Russel D. W., ed., Molecular Cloning, Third Ed., Cold Spring Harbor Laboratory Press etc.) on gene recombinant technology can be used. As the general method, there can be mentioned a method of ligating with restriction enzyme cleavage sites. When restriction enzyme recognition sites are not available, such sites may be introduced by polymerase chain reaction (PCR), in vitro mutation or the like.

Recombinant Herpesvirus

The recombinant herpesvirus of the present invention must employ a herpesvirus other than ILTV as the parent virus. The parent herpesvirus may be any herpesvirus that infects mammals or avians. However, as the integrated gene cannot stably exist in ILTV, ILTV cannot be used as the parent virus. When a vaccine for avians is to be obtained, it is preferred to select Marek's disease virus as the parent herpesvirus. There are three types of Marek's disease virus: type 1, 2 and 3, and any type can be selected in accordance with the present invention. A Marek's disease virus may be naturally obtained, or is available from ATCC etc., with or without cost, and non-pathogenic ones are preferred. As such viruses, there can be mentioned, for example, the CV1988 (Rispens) strain as Marek's disease virus type 1, the SB-1 strain as the Marek's disease virus type 2, and FC126 (ATCC VR-584B), PB-THV1, H-2, YT-7 and HPRS-26 as Marek's disease viruses type 3.

The method of constructing a recombinant herpesvirus is not specifically limited, and a recombinant plasmid having an additive DNA ligated as desired to the above-mentioned partial gB gene may be used, which may be inserted into a parent herpesvirus by homologous recombination. At this time, the partial gB gene is located at a position that is under the control of a foreign or endogenous promoter.

As a plasmid for use as a recombinant plasmid (hereinafter referred to as homology vector), any commonly used one can be used and includes, for example, pBR322, pBR325, pBR327, pBR328, pUC8, pUC18 and pUC19.

The construction of a homology vector may be performed according to a standard method using restriction enzyme sites owned by the vector.

The homology vector is a plasmid in which, usually, the promoter and the polyA signal are added to the above-mentioned partial gB gene which is then inserted into a region nonessential for the growth of the recombinant herpesvirus.

The method of constructing the homology vector of the present invention will be explained hereinbelow.

When DNA is to be integrated into a recombinant herpesvirus, it is generally integrated so that the DNA molecule of the present invention is located under the control of a regulatory gene (promoter) in order to obtain high expression. The promoter may be any commonly used one that operates in an eukaryotic cell, and may be derived from an eukaryotic cell or from a virus. Specific examples of the promoter include the thymidine kinase promoter of herpesvirus (Ross et al., J. Gen. Virol. 74:371-377, 1993), the gB protein promoter of turkey herpesvirus (HVT) and Marek's disease virus (MDV) type 1 (Ross et al., J. Gen. Virol. 74:371-377, 1993), the IE promoter of human cytomegalovirus (HCMV) (Stinski et al., J. Virol. 55:431-441, 1985), the SV40 promoter (Gunning et al., Proc. Natl. Acad. Sci. U.S.A. 84:4831-4835, 1987), the human β-acting promoter (Gunning et al., Proc. Natl. Acad. Sci. U.S.A. 84:4831-4835, 1987), the chicken β-actin promoter (Kost et al., Nucleic Acids Res. 11:8287-8301, 1983), the LTR promoter of Rous sarcoma virus (RSV) (Greuel et al., Virology 177:33-43, 1990), the Pec promoter (Japanese Unexamined Patent Publication (Kokai) No. 2001-000188) and the like.

By adding an enhancer which is a transcription-activating factor in addition to the promoter, a further effective expression may be expected (Stinski et al., J. Virol. 55:431-441, 1985). As the enhancer, part of the cytomegalovirus-derived promoter may be illustrated and, generally, the positional relationship to the inserted gene is not limited. As the promoter of this type, there can be illustrated the Pec promoter described in Japanese Unexamined Patent Publication (Kokai) No. 2001-000188.

Furthermore, by adding a polyadenylation signal downstream to the additive DNA, a specifically high expression may be expected.

As the polyadenylation signal, there can be illustrated a polyA signal such as SV40 (Gunning et al., Proc. Natl. Acad. Sci. U.S.A. 84:4831-4835, 1987) and the polyA signal of UL46h, UL47h and UL49h of Marek's disease virus (MDV) type 1 (Yanagida et al., J. Gen. Virol. 74:1837-1845, 1993).

As the gene regions nonessential for the growth of herpesvirus in the case of Marek's disease virus (MDV) type 1, type 2 and type 3 (type 3 is the turkey herpesvirus), there can be illustrated the TK region (Ross et al., the 16th International Herpes Workshop, 1991), the US10 region (Sakaguchi et al., Vaccine 12:953-957, 1994), the US2 region (Sondermeijer, P. J. et al., Vaccine 11:349-358, 1993), the region between UL44 and 45 and between UL45 and 46 described in Japanese Unexamined Patent Publication (Kokai) No. 11-192093, and the like.

The homology vector may be constructed by inserting a foreign gene such as the partial gB gene or the additive DNA, an exemplary DNA of the present invention. The length of the nonessential region into which foreign genes such as DNA of the present invention is inserted is not specifically limited, but 10 bp or more forward or behind the foreign gene insertion site, preferably 100 bp or more, and more preferably 500 bp or more of bases derived from the nonessential region is sufficient.

By the homologous recombination of the above-mentioned homology vector and the parent herpesvirus, a recombinant herpesvirus can be obtained.

As a concrete method of constructing a recombinant herpesvirus, the following method can be illustrated.

The homology vector is introduced into a herpesvirus-infected cell by electroporation, the calcium phosphate method, a method using lipofectin, a method using a gene gun and the like. For example, when the parent virus is an avian herpesvirus, the cell to be infected by the herpesvirus is preferably an avian-derived cell such as a chick embryo fibroblast (CEF), a developing chicken egg, a chicken kidney cell etc. The infected cell may be cultured by a commonly used culture method. As a method of introducing the homology vector into the infected cell, electroporation or a method using lipofectin is preferably adopted for the purpose of obtaining a high introduction efficiency. When the amount of the homology vector (plasmid etc.) to be introduced is in the range of 0.1-1000 µg, incidences of forming a recombinant herpesvirus from the homologous regions of the herpesvirus genomic DNA and the homology vector become high. As a method of selecting only such a recombinant herpesvirus to which such a homology vector has been introduced, the black plaque assay (BPA) method can be used. In the BPA method, an immunological reaction is carried out using an antibody against the foreign gene, and plaques that expressed the foreign antigen are visualized, that is, an antibody against the foreign gene is used and then an enzyme-labelled secondary antibody is used, and finally a substrate corresponding to the enzyme is used for visualization. By this method, a recombinant herpesvirus that expressed the foreign gene is selected. Furthermore, it has an advantage that, when such a recombinant herpesvirus is constructed, the detection of integration can be easily carried out using a marker gene such as β-galactosidase as the foreign gene. When the β-galactosidase gene is used, a recombinant can be easily isolated by monitoring the expression using Bluo-Gal (Invitrogen) etc. Otherwise, a method such as plaque hybridization may be used to isolate the desired recombinant herpesvirus. By repeating these procedures, recombinant herpesvirus can be purified.

Vaccine for Infectious Laryngotracheitis Virus

The vaccine of the present invention for infectious laryngotracheitis virus is a vaccine for avians comprising as an active ingredient the above recombinant herpesvirus of the present invention.

The method of preparing the vaccine is not specifically limited, and may be prepared by, for example, the following method.

The cells infected with the recombinant herpesvirus of the present invention are infected to the cells (hereinafter referred to as the host cell) in which said virus can grow, and after the viruses are grown cells are scraped by a scraper or trypsin, followed by centrifugation to separate the infected cells and the supernatant. For example, when the parent virus is an avian herpesvirus, an avian-derived cell is preferred as the host cell, and chick embryo fibroblasts (CEF), chicken kidney cells etc. can be suitably used. The infected cells obtained are suspended in a culture medium containing 10% dimethyl sulfoxide (DMSO) and stored frozen in liquid nitrogen. When they are used as the vaccine, a suitable amount of phosphate buffer or physiological saline is used to dissolve the lyophilized product before use.

Stabilizers or other ingredients for storing the above infected cells under liquid nitrogen are any ingredients that allow stable survival of the virus-infected cells and that are not pharmacologically harmful to the recipient.

The method of administering the vaccine comprising as an main ingredient the recombinant herpesvirus thus prepared to avians is not specifically limited. For example, there can be mentioned the same method currently used for herpesvirus vaccines such as a method of injecting subcutaneously to an individual avian and a method of inoculating by puncturating a growing egg.

The amount inoculated and the timing of inoculation may the same as those used for the current vaccines. For example, by inoculating a dose of $10^2$-$10^5$ PFU or $10^2$-$10^4$ TCID$_{50}$ subcutaneously on the back of an avian on the day of hatching using a 20G or larger needle, the effect as vaccine can be expected. Or the same dose as above may be inoculated by puncturating a developing egg on day 18-19 after development. In addition to the method of administering to avians using a needle as the method of inoculation, an in ovo inoculation instrument such as Inovoject (Embrex) may be used.

The recombinant herpesvirus obtained as above functions not only as a vaccine against ILTV but as a vaccine against the parent herpesvirus as well.

EXAMPLES

Example 1

Construction of a Recombinant Plasmid (Homology Vector) Having the Full-length ILTV gB Gene A BglII-cleaved 125 bp fragment of pGHMCSpolyASfi described in U.S. Pat. Pub. No. 2003-0059799 was inserted into the SfiI fragment of pNZ45/46Sfi described in International Patent Publication WO99/18215 (EP1026246) to construct P45/46HMCSpolyASfi. With pUC18Xlac described in International Patent Publication WO98/18215 (EP1026246) as the template, PCR was carried out using a primer M13(-21) set forth in SEQ ID NO: 6 and a primer lac3'KpnR set forth in SEQ ID NO: 7 to obtain a 3205 bp fragment.

PCR used the Pfu polymerase (Stratagene Corp.) and the DNA Thermal Cycler 480 of Perkin Elmer Inc. and was carried out for 30 cycles under a standard condition (denaturation at 95° C. for 1 min, annealing at 60° C. or 55° C. for 2 minutes, and extension at 72° C. for 3 minutes). This condition was used in all Examples unless otherwise specified.

A 3149 bp fragment obtained by digesting the PCR-amplified 3205 bp fragment with BamHI and KpnI was ligated to a 5573 bp fragment obtained by digesting P45/46HMCSpolyASfi with BamHI and KpnI to construct pNZ45/46HlacpolyASfi.

On the other hand, with pBK—CMV (Stratagene Corp.) as the template, PCR was carried out using a primer M13(-21) set forth in SEQ ID NO: 6 and a primer pCMV-1 set forth in SEQ ID NO: 8 to obtain a 953 bp fragment. A 599 bp fragment obtained by digesting this 953 bp fragment with PstI and NheI, a 382 bp fragment obtained by digesting pNZ45/46HlacpolyASfi with PstI and SphI and a 8332 bp fragment obtained by digesting pNZ45/46HlacpolyASfi with SphI and XbaI were subjected to three-fragment ligation to construct pNZ45/46HCMVlac.

In order to delete the BglII cleavage site in the ILTV gB gene without changing the encoding amino acids, two fragments were obtained with pGTPs/ILgB described in Japanese Unexamined Patent Publication (Kokai) No. 10-807866 (EP953642) as the template, a 1132 bp fragment obtained by PCR amplification using a primer ILgB-5 set forth in SEQ ID NO: 9 and a primer ILgB-BglR set forth in SEQ ID NO: 10, and a 1564 bp fragment obtained by PCR amplification using a primer ILgB-Bgl set forth in SEQ ID NO: 11 and a primer ILgB-3+Kpn set forth in SEQ ID NO: 12. With the two fragments as the template, PCR was carried out using a primer ILgB-5 set forth in SEQ ID NO: 9 and a primer ILgB-3+Kpn set forth in SEQ ID NO: 12 to obtain a 2648 bp fragment. A 2638 bp fragment obtained by digesting this 2648 bp fragment with BamHI and KpnI and a 3280 bp fragment obtained by digesting pGIPec described in Japanese Unexamined Patent Publication (Kokai) No. 2001-000188 with BamHI and KpnI were ligated to construct pGIPecILgB.

A 2638 bp fragment obtained by digesting this pGIPecILgB with BamHI and KpnI and a 4479 bp fragment obtained by digesting pGIBacpA described in EP1298139 with BamHI and KpnI were ligated to construct pGIBAcgBpA.

By inserting a 4464 bp fragment obtained by digesting this pGIBAcgBpA with BglI into the SfiI site of the above pNZ45/46HCMVlac, a homology vector p45/46HCMVlacBacgB2nd having CMV-IE as the promoter was constructed.

Then, in order to delete the BglI cleavage site in the CMV promoter, a primer pCMV-1 set forth in SEQ ID NO: 8 and a primer pPec1R set forth in SEQ ID NO: 13 were amplified by PCR with pGIPec described in Japanese Unexamined Patent Publication (Kokai) No. 2001-000188 as the template to obtain a 293 bp fragment. With pBK-CMV (Stratagene Corp.) as the template, a primer pCMV-o1 set forth in SEQ ID NO: 14 and a primer pCMV-R1 set forth in SEQ ID NO: 15 were used in PCR amplification to obtain a 341 bp fragment. With these two fragments as the template, a primer pCMV-1 set forth in SEQ ID NO: 8 and a primer pCMV-R1 set forth in SEQ ID NO: 15 were used in PCR amplification to obtain a 604 bp fragment. A 589 bp fragment obtained by digesting this 604 bp fragment with PstI and XbaI and a 2765 bp fragment obtained by digesting pGIPec described in Japanese Unexamined Patent Publication (Kokai) No. 2001-000188 with PstI and XbaI were ligated to construct pGICMV(−).

A 2137 bp fragment obtained by digesting this pGICMV (−) with BamHI and XhoI and a 4054 bp fragment obtained by digesting the above pGIBAcgBpA with BamHI and XhoI were ligated to construct pCMV-ILgB. By inserting a 3338 bp fragment obtained by digesting this pCMV-ILgB with BglI into the SfiI site of pNZ45/46RSVlac-T, a homology vector p45/46CMVILgBlac, having CMV-IE as the promoter, was constructed.

A 2103 bp fragment obtained by digesting pGIPec described in Japanese Unexamined Patent Publication (Kokai) No. 2001-000188 with BamHI and XhoI and a 4054 bp fragment obtained by digesting the above pGIBAcgBpA with BamHI and XhoI were ligated to construct pGIPecILgB2.

By inserting a 3504 bp fragment obtained by digesting this pGIPecILgB2 with BglI into the SfiI site of pNZ45/46RSVlac-T described in Japanese Unexamined Patent Publication (Kokai) No. 11-192093 (EP1026246), a homology vector p45/46PecILgBlac having the Pec promoter as the promoter was constructed.

Similarly, by inserting a 3504 bp fragment obtained by digesting the above pGIPecILgB2 with BglI into the SfiI site of pNZ45/46Sfi described in Japanese Unexamined Patent Publication (Kokai) No. 11-192093 (EP1026246), a homology vector p45/46PecILgB having the Pec promoter as the promoter was constructed.

Example 2

Construction and Purification of a Recombinant HVT Having a Full-length ILTV gB Gene Using the four homology vectors (p45/46HCMVlacBacgB2nd, p45/46CMVILgBlac, p45/46PecILgBlac, p45/46PecILgB) constructed in Example 1, a recombinant HVT was constructed and purified.

Specifically the following procedure was carried out.

First, the DNA of HVT was collected according to the method of Morgan et al. (Avian Dis., Vol. 34, 345-351, 1990). Thus, about $1\times10^5$ PFU of HVT, the FC126 strain (ATCC VR-584B) or the FC126 strain (the original strain provided by Dr. Witter) was infected to about $3\times10^7$ CEF, and after culturing for 2-3 days, 4 ml of the lysis buffer (0.5% SDS, 10 mM Tris (pH8.0), 100 mM NaCl, 1 mM EDTA, 200 μg/ml proteinase K) was added thereto and incubated at 37° C. for 4 hours, followed by phenol extraction and ethanol precipitation to collect HVT-DNA.

The homology vectors were cleaved with restriction enzymes at regions containing no homologous sites or foreign genes and linearized.

About $3\times10^6$ CEF collected with trypsin was suspended into saline G (0.14 M NaCl, 0.2 mM KCl, 1.1 mM disodium hydrogen phosphate, 1.5 mM monobasic potassium phosphate, 0.5 mM magnesium chloride hexahydrate, 0.011% glucose), 10-30 μg of the above HVT-DNA and 10-30 μg of a linearized homology vector for recombination were each electroporated using the gene pulser (manufactured by Bio-Rad Inc.) under the condition of 0.5 $KVcm^{-1}$ and 0.4 msec. The cell suspension was plated on a culture dish with a diameter of 6 cm, and after adding a culture medium, it was cultured for 5-7 days. After culturing, the virus containing the recombinant HVT was collected from the culture liquid. Then the limiting dilution was carried out to purify recombinant HVT.

The specific method of purification was as follows:

For the homology vector p45/46PecILgB containing no lacZ gene, about $2\times10^6$ CEF together with the serially diluted virus solution were plated on 96-well plates. After culturing for 3-5 days, plaques appeared, and a replica was prepared. One of the plates was subjected to screening according to the Black Plaque Assay (BPA) as follows:

Antiserum (anti-ILTV-gB antiserum) obtained by immunizing a rabbit with the ILTV-gB protein expressed in *Escherichia coli* diluted about 500-fold in a Dulbecco's phosphate buffer (manufactured by Dainippon Seiyaku Co., Ltd.; hereinafter referred to as PBS(−)) containing no magnesium was reacted to plaques at 22-25° C. for 2 hours. After washing with 3% non-fat dried milk in PBS(−) three times, it was reacted to plaques at 22-25° C. for 2 hours with biotinylated anti-rabbit antibody (sheep, Biosource Inc.). The antibody after the reaction was washed in PBS(−), and then reacted to avidin-biotin-alkaline phosphatase complex (Vector laboratories). After rinsing off the unreacted avidin-biotin-alkaline phosphatase complex with PBS(−), the color was allowed to change from dark blue to black using BCIP/NBT (manufactured by Roche), a substrate for alkaline phosphatase.

In the BPA method, the suspended virus corresponding to positive plaques thus generated is infected again to CEF, and this procedure is repeated for 3-4 times until all plaques become positive with BPA and, usually, the purification and construction of recombinant HVT is complete.

However, for recombinant HVT that has integrated p45/46PecILgB, recombinant HVT that was purified to 100% could not be obtained.

The construction of recombinant HVT using the homology vectors p45/46HCMVlacBacgB2nd, p45/46CMVILgBlac and p45/46PecILgBlac containing lacZ was carried out according to the following procedure.

Thus, about $2\times10^6$ CEF together with the serially diluted virus solutions were plated on 96-well multi plates. After culturing for 3-5 days, plaques appeared, and a replica was prepared. To one of the plates, 100 μl/well each of 100 μg/ml Bluo-gal (manufactured by Gibco), a chromogenic substrate for β-galactosidase, was added, and incubated at 37° C. for 4 hours. As plaques that express lacZ turn blue, cells were collected from those wells in another plate corresponding to wells that contain blue-colored plaques to make it a virus solution. This virus solution was plated together with about $2\times10^6$ CEF on a flat-bottomed 96-well multi plate for culturing. A step of subculturing from a flat-bottomed 96-well multi plate for culturing to a flat-bottomed 96-well multi plate for culturing was considered to be one screening. Screening was repeated until all wells had blue plaques, and purification was carried out until all plaques turned blue (usually about 5-10 times of screening) when Bluo-gal was added.

As a result, one clone of recombinant HVT was successfully purified only from the homology vector p45/46PecILgBlac, and this was named FW050.

When p45/46HCMVlacBacgB2nd or p45/46CMVILgBlac was used, no 100%-purified recombinant HVT was obtained.

Example 3

The Structure and Vaccine Effect of Recombinant HVT FW050

FW050, a recombinant HVT obtained in Example 2, was directly sequenced. The result revealed that FW050 has a deletion of 1542 bp containing the polyA signal, and instead three bases (GCG) of unknown origin have been sandwiched (SEQ ID NO: 22). As a result, it was predicted to express a chimera protein consisting of 469 amino acids that comprises 429 amino acids at the amino terminal end of the ORF of the original ILTV gB gene and 40 amino acids that are now encoded by the polyA signal portion until the stop codon appears (see FIG. 1 and SEQ ID NO: 1).

This FW050 was subjected to an animal experiment for examining the vaccine effect and the result shown in Table 1 was obtained.

The animal experiment was carried out according to the provisions (9CFR) in the Animal and Plant Health Inspection Service (APHIS) by the Department of Agriculture of the USA.

Challenge of an highly toxic ILTV was carried out using a method described in 9CFR Ch.1 113.328. Thus, a recombinant HVT was inoculated to over 10 SPF chickens per group (Line M: Nippon Institute for Biological Science) (In Experiment 1 alone, the number of inoculated chickens for FW050 was 9 due to the accidental death of one animal after inoculation). The negative control group (control) received no inoculation.

When the test SPF chickens hatched, recombinant HVT was subcutaneously inoculated to the back of chickens at $1\times10^4$ PFU using a 26G needle. To 4 week-old animals, a ml) was challenge-inoculated to the infraorbital groove. For ten days after inoculation, clinical symptoms were daily observed and the presence or absence of infection prevention was determined.

The result is shown in Table 1.

As can be seen from Table 1, a protective effect against the highly virulent ILTV strain was recognized for FW050.

TABLE 1

| | Recombinant HVT | Homology vector | Protection rate % (No. of chickens protected/total No. of chickens) Experiment 1 | Experiment 2 |
|---|---|---|---|---|
| Control | | | 0 (0/10) | 0 (0/16) |
| Challenge | FW050 | p45/46PecILgBlac | 78 (7/9) | 31 (4/13) |

Example 4

Construction of a Recombinant Having a Fragment in Which the gB Gene of ILTV was Truncated A homology vector having a mutant gB gene product in which part of ORF of the ILTV gB gene was deleted was constructed as follows:

(1) A homology vector that contains DNA encoding 623-amino acid gB-a from the amino terminal that is the ORF of the ILTV gB gene and that is unlikely to contain a dimer-forming region: p45/46PecILgBa and p45/46PecILgBalac Using pGIPecILgB2 constructed in Example 1 as the template, a 1205 bp fragment was amplified by the above-mentioned standard PCR using a primer P-BglII set forth in SEQ ID NO: 16 and a primer A-R set forth in SEQ ID NO: 17. A 1198 bp fragment obtained by digesting this with BglII and KpnI and a 7057 bp fragment obtained by digesting p45/46PecILgB constructed in Example 1 with BglII and KpnI were ligated to construct a homology vector p45/46PecILgBa.

A 6373 bp fragment obtained by digesting p45/46PecILgBa with BglII and XhoI and a 5923 bp fragment obtained by digesting p45/46PecILgBlac constructed in Example 1 with BglII and XhoI were ligated to construct a homology vector p45/46PecILgBalac.

(2) A homology vector that contains DNA encoding 691-amino acid gB-b in which the carboxy terminal has been deleted to immediately before the transmembrane domain: p45/46PecILgBb and p45/46PecILgBblac Using pGIPecILgB2 constructed in Example 1 as the template, a 1409 bp fragment was amplified by the above-mentioned standard PCR using a primer P-BglII set forth in SEQ ID NO: 16 and a primer B-R set forth in SEQ ID NO: 18. A 1402 bp fragment obtained by digesting this with BglII and KpnI and a 7057 bp fragment obtained by digesting p45/46PecILgB constructed in Example 1 with BglII and KpnI were ligated to construct a homology vector p45/46PecILgBb.

A 6577 bp fragment obtained by digesting p45/46PecILgBb with BglII and XhoI and a 5923 bp fragment obtained by digesting p45/46PecILgBlac constructed in Example 1 with BglII and XhoI were ligated to construct a homology vector p45/46PecILgBblac.

(3) A homology vector that contains DNA encoding 803-amino acid gB-c in which the transmembrane domain alone has been deleted: p45/46PecILgBc and p45/46PecILgBclac Using pGIPecILgB2 constructed in Example 1 as the template, a 1409 bp fragment was amplified by the above-mentioned standard PCR using a primer P-BglII set forth in SEQ ID NO: 16 and a primer C-R set forth in SEQ ID NO: 19. Similarly, using pGIPecILgB2 as the template, a 357 bp fragment was amplified by the standard PCR using a primer C-F set forth in SEQ ID NO: 20 and a primer CDE-R set forth in SEQ ID NO: 21. Using two fragments of the 1409 bp fragment and the 357 bp fragment as the template, a 1745 bp fragment was amplified by the standard PCR using a primer P-BglII set forth in SEQ ID NO: 16 and a primer CDE-R set forth in SEQ ID NO: 21. A 1738 bp fragment obtained by digesting this with BglII and KpnI and a 7057 bp fragment obtained by digesting p45/46PecILgB constructed in Example 1 with BglII and KpnI were ligated to construct a homology vector p45/46PecILgBc.

A 6913 bp fragment obtained by digesting p45/46PecILgBc with BglII and XhoI and a 5923 bp fragment obtained by digesting p45/46PecILgBlac constructed in Example 1 with BglII and XhoI were ligated to construct a homology vector p45/46PecILgBclac.

Figure 1:
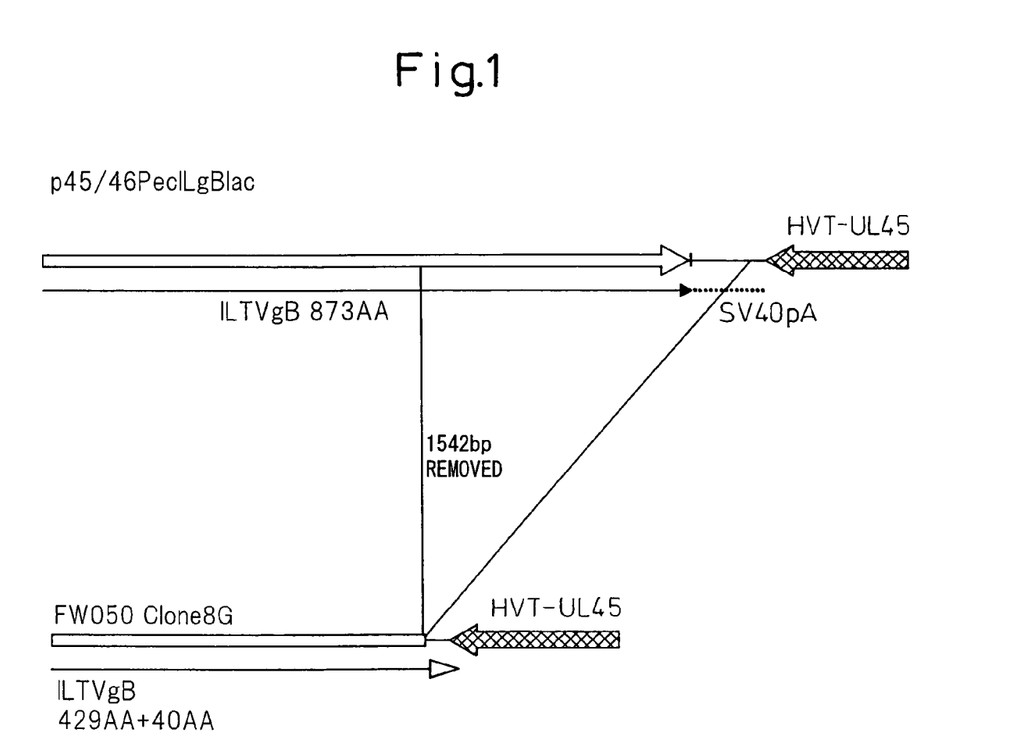
FIG. 1 is a drawing that compares FW050 with the original homology vector.
Figure 2:
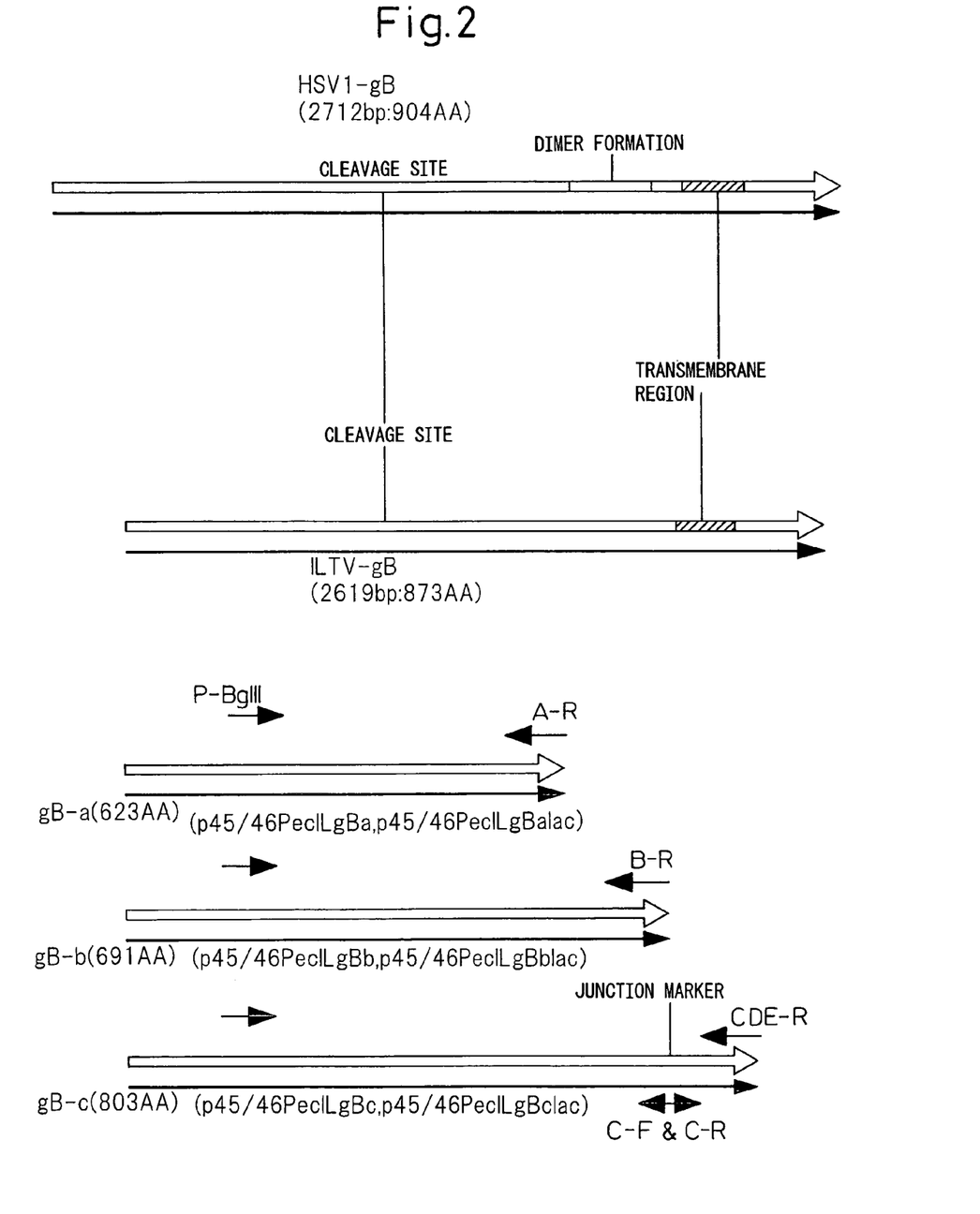
FIG. 2 is a schematic diagram of the homology vector.

The schematic diagrams of these homology vectors are shown in FIG. 2.

Using these six homology vectors, thus constructed, purification of recombinant HVTs were attempted in a manner similar to that described in Example 2, but recombinants having the same structure as the homology vectors could not be obtained.

Thus, though a plurality of homology vectors were constructed that were truncated from the carboxy terminal of the gB protein subsequent to the promoter to purify and construct recombinant HVT, recombinants having the same length of the ILTV gB gene as the homology vectors could not be obtained. This result demonstrated that when the gB gene integrated together with the promoter was to be expressed in recombinant HVT, those having a long ORF cannot be purified. Also, even if recombinant HVT could be purified, it was thought, the ORF of the gB gene in the recombinant HVT obtained becomes curtailed due to selection pressure. Thus, it was predicted that when the gB gene is integrated together with the promoter, the length of gB gene ORF of ILTV that can be present as a stable recombinant HVT is about the size of those encoding 623 amino acids or shorter.

Example 5

Modification from the Deleted Clone FW050 was Reverted and the Vaccine Effect of the Recombinant HVT From the recombinant HVT FW050 for which the vaccine effect was confirmed in Example 3 and which is expected to express a fusion protein of the 429 amino acids from the amino terminal end of the gB protein of ILTV and the 40 amino acids derived from polyA, a homology vector p45/46CMVILgBf was constructed in order to express a protein in which 40 amino acids derived from polyA of the protein to be expressed have been deleted.

Specifically, a 303 bp fragment obtained by digesting pGI-BacpA described in Japanese Unexamined Patent Publication (Kokai) No. 2004-000111 with EcoRI and KpnI and a 5854 bp fragment obtained by digesting pGIPecILgB2 constructed in Example 1 with EcoRI and KpnI were ligated to construct pGIPecILgB3. A 2245 bp fragment obtained by digesting this pGIPecILgB3 with BglII and SfiI and a 6759 bp fragment obtained by digesting p45/46PecILgB with BglII and SfiI were ligated to construct p45/46PecILgB2.

Then, using pGIPecILgB2 as the template, P-BglII set forth in SEQ ID NO: 16 and F-R set forth in SEQ ID NO: 23 were subjected to PCR to obtain a 623 bp fragment. A 616 bp fragment obtained by digesting this with BglII and KpnI and a 7057 bp fragment obtained by digesting p45/46PecILgB2 with BglII and KpnI were ligated to construct p45/46PecILgBf.

A 7102 bp fragment obtained by complete digestion of this p45/46PecILgBf with XbaI followed by partial digestion with PstI and a 589 bp fragment obtained by digesting pGICMV(−) constructed in Example 1 with PstI and XbaI were ligated to complete the construction of a homology vector p45/46CMVILgBf.

Using this homology vector p45/46CMVILgBf, FW063, a recombinant HVT, was constructed and purified. It was confirmed that the inserted gene portion of the recombinant HVT FW063 was the same as the base sequence of the homology vector and had not been mutated.

Furthermore, by reversely cloning FW050, a homology vector p45/46PecILgBdellac was constructed in the following procedure.

The template used in PCR for this cloning is a viral DNA collected from a chicken that was inoculated with FW050, and the primer was two primers of P-BglII set forth in SEQ ID NO: 16 and 45/46F(K) set forth in SEQ ID NO: 24, and the homology vector p45/46PecILgBdellac was constructed by ligating a 707 bp fragment obtained by digesting, with BglII and SfiI, a 944 bp fragment obtained by amplification with the two primers and a 10809 bp fragment obtained by digesting p45/46PecILgBelac with BglII and SfiI. Using this homology vector p45/46PecILgBdellac, recombinant HVT FW069 was successfully purified and constructed.

In the same manner as above, without changing the polyA portion at all, a homology vector p45/46PecILgBdellac+STP in which termination was inserted into a site where the ORF of 429 amino acids at the amino terminal end of the gB protein terminated was constructed in the following procedure.

First, using, as the template, a 637 bp fragment amplified using a primer P-BglII set forth in SEQ ID NO: 16 and a primer gBdelSTP-R set forth in SEQ ID NO: 25 and a 673 bp fragment amplified using a primer gBdelSTP-F set forth in SEQ ID NO: 26 and a primer 45/46F(B) set forth in SEQ ID NO: 27, PCR was carried out with the primer PBglII and the primer 45/46F(B) to obtain a 1263 bp fragment. Then a 707 bp fragment obtained by digesting this with BglII and SfiI and a 10809 bp fragment obtained by digesting p45/46PecILg-Blac with BglII and SfiI were ligated to construct a homology vector p45/46PecILgBdellac+STP.

Using this homology vector p45/46PecILgBdellac+STP, a recombinant HVT FW070 was successfully purified and constructed.

Thus, FW063, FW069 and FW070, in which the ORF of the gB gene is 429 amino acids as in FW050 described in Example 3, could easily be purified. This demonstrated that when DNA derived from the gB gene encoding the 429 amino acids at the amino terminal end of the amino acid sequence set forth in SEQ ID NO: 2 is to be expressed in a recombinant HVT that has integrated it together with the promoter, purification can be carried out.

Using the recombinant HVT thus purified, FWO063, FW069 and FW050 purified in Example 3, a challenge test was carried out as in Example 3 to investigate the vaccine effect. The result is shown in Table 2.

TABLE 2

|  | Recombinant HVT | Homology vector | Protection rate % (No. of chickens protected/ total No. of chickens) |
| --- | --- | --- | --- |
| Control |  |  | 0 (0/7) |
| Challenge | FW050 | p45/46PecILgBlac | 54 (7/13) |
| Challenge | FW063 | p45/46CMVILgBf | 33 (5/15) |
| Challenge | FW069 | p45/46PecILgBdellac | 56 (9/16) |

From the result, it can be seen that the vaccine effect can also be recognized for FW063 having no additive sequence, and FW069 and FW050 that have the additive sequence exhibit a better vaccine effect.

---

The invention claimed is:

1. A recombinant herpesvirus that is not infectious laryngotracheitis virus, wherein the recombinant herpesvirus has a DNA that encodes the polypeptide of SEQ ID NO: 2, but that does not encode any other portion of the gB protein of infectious laryngotracheitis virus.

2. The recombinant herpesvirus according to claim 1 in which a DNA encoding the amino acid sequence set forth in SEQ ID NO: 4 is linked in a frame with the 3'-end of the DNA encoding the polypeptide of SEQ ID NO: 2.

3. A recombinant herpesvirus according to claim 2, wherein the herpesvirus is a herpesvirus that infects avians.

4. The recombinant herpesvirus according to claim 3 wherein the herpesvirus is Marek's disease virus type 1, 2 or 3.

5. A vaccine against infectious laryngotracheitis virus comprising as an active ingredient a recombinant herpesvirus according to claim 4.

6. The recombinant herpesvirus according to claim 1, wherein the herpesvirus is a herpesvirus that infects avians.

7. The recombinant herpesvirus according to claim 6 wherein the herpesvirus is Marek's disease virus type 1, 2 or 3.

8. A vaccine against infectious laryngotracheitis virus comprising as an active ingredient a recombinant herpesvirus according to claim 7.

9. A vaccine against infectious laryngotracheitis virus comprising as an active ingredient a recombinant herpesvirus according to claim 6.

10. A vaccine against infectious laryngotracheitis virus comprising as an active ingredient a recombinant herpesvirus according to claim 1.

11. A vaccine against infectious laryngotracheitis virus comprising as an active ingredient a recombinant herpesvirus according to claim 2.

12. A vaccine against infectious laryngotracheitis virus comprising as an active ingredient a recombinant herpesvirus according to claim 3.

* * * * *

SEQUENCE LISTING

<160> NUMBER OF SEQ ID NOS: 27

<210> SEQ ID NO 1
<211> LENGTH: 469
<212> TYPE: PRT
<213> ORGANISM: Artificial
<220> FEATURE:
<223> OTHER INFORMATION: Infecitous laryngotracheitis virus and artificial ORF

<400> SEQUENCE: 1

Met Ala Ser Leu Lys Met Leu Ile Cys Val Cys Val Ala Ile Leu Ile
1               5                   10                  15

Pro Ser Thr Leu Ser Gln Asp Ser His Gly Ile Ala Gly Ile Ile Asp
            20                  25                  30

Pro Arg Asp Thr Ala Ser Met Asp Val Gly Lys Ile Ser Phe Ser Glu
        35                  40                  45

Ala Ile Gly Ser Gly Ala Pro Lys Glu Pro Gln Ile Arg Asn Arg Ile
    50                  55                  60

Phe Ala Cys Ser Ser Pro Thr Gly Ala Ser Val Ala Arg Leu Ala Gln
65                  70                  75                  80

Pro Arg His Cys His Arg His Ala Asp Ser Thr Asn Met Thr Glu Gly
                85                  90                  95

Ile Ala Val Val Phe Lys Gln Asn Ile Ala Pro Tyr Val Phe Asn Val
            100                 105                 110

Thr Leu Tyr Tyr Lys His Ile Thr Thr Val Thr Thr Trp Ala Leu Phe
        115                 120                 125

Ser Arg Pro Gln Ile Thr Asn Glu Tyr Val Thr Arg Val Pro Ile Asp
    130                 135                 140

Tyr His Glu Ile Val Arg Ile Asp Arg Ser Gly Glu Cys Ser Ser Lys
145                 150                 155                 160

Ala Thr Tyr His Lys Asn Phe Met Phe Phe Glu Ala Tyr Asp Asn Asp
                165                 170                 175

Glu Arg Glu Lys Lys Leu Pro Leu Val Pro Ser Leu Leu Arg Ser Thr
            180                 185                 190

Val Ser Lys Ala Phe His Thr Thr Asn Phe Thr Lys Arg His Gln Thr
        195                 200                 205

Leu Gly Tyr Arg Thr Ser Thr Ser Val Asp Cys Val Val Glu Tyr Leu

```
              210                 215                 220
Gln Ala Arg Ser Val Tyr Pro Tyr Asp Tyr Phe Gly Met Ala Thr Gly
225                 230                 235                 240

Asp Thr Val Glu Ile Ser Pro Phe Tyr Thr Lys Asn Thr Thr Gly Pro
            245                 250                 255

Arg Arg His Ser Val Tyr Arg Asp Tyr Arg Phe Leu Glu Ile Ala Asn
            260                 265                 270

Tyr Gln Val Arg Asp Leu Glu Thr Gly Gln Ile Arg Pro Lys Lys
            275                 280                 285

Arg Asn Phe Leu Thr Asp Glu Gln Phe Thr Ile Gly Trp Asp Ala Met
290                 295                 300

Glu Glu Lys Glu Ser Val Cys Thr Leu Ser Lys Trp Ile Glu Val Pro
305                 310                 315                 320

Glu Ala Val Arg Val Ser Tyr Lys Asn Ser Tyr His Phe Ser Leu Lys
            325                 330                 335

Asp Met Thr Met Thr Phe Ser Ser Gly Lys Gln Pro Phe Asn Ile Ser
            340                 345                 350

Arg Leu His Leu Ala Glu Cys Val Pro Thr Ile Ala Ser Glu Ala Ile
            355                 360                 365

Asp Gly Ile Phe Ala Arg Lys Tyr Ser Ser Thr His Val Arg Ser Gly
            370                 375                 380

Asp Ile Glu Tyr Tyr Leu Gly Ser Gly Gly Phe Leu Ile Ala Phe Gln
385                 390                 395                 400

Lys Leu Met Ser His Gly Leu Ala Glu Met Tyr Leu Glu Glu Ala Gln
                405                 410                 415

Arg Gln Asn His Leu Pro Arg Gly Arg Glu Arg Gln Gly Asp Leu
                420                 425                 430

Tyr Lys Cys Gly Met Ala Asp Tyr Asp His Glu Gln Thr Val Arg Thr
            435                 440                 445

Glu Gly Pro Glu Met Ser Leu Gly Thr Val Asn Arg Pro Ile Arg Pro
450                 455                 460

Ile Tyr Ser Ser His
465

<210> SEQ ID NO 2
<211> LENGTH: 429
<212> TYPE: PRT
<213> ORGANISM: Infectious laryngotracheitis virus

<400> SEQUENCE: 2

Met Ala Ser Leu Lys Met Leu Ile Cys Val Cys Val Ala Ile Leu Ile
1               5                   10                  15

Pro Ser Thr Leu Ser Gln Asp Ser His Gly Ile Ala Gly Ile Ile Asp
            20                  25                  30

Pro Arg Asp Thr Ala Ser Met Asp Val Gly Lys Ile Ser Phe Ser Glu
            35                  40                  45

Ala Ile Gly Ser Gly Ala Pro Lys Glu Pro Gln Ile Arg Asn Arg Ile
        50                  55                  60

Phe Ala Cys Ser Ser Pro Thr Gly Ala Ser Val Ala Arg Leu Ala Gln
65              70                  75                  80

Pro Arg His Cys His Arg His Ala Asp Ser Thr Asn Met Thr Glu Gly
                85                  90                  95

Ile Ala Val Val Phe Lys Gln Asn Ile Ala Pro Tyr Val Phe Asn Val
            100                 105                 110
```

```
Thr Leu Tyr Tyr Lys His Ile Thr Thr Val Thr Thr Trp Ala Leu Phe
            115                 120                 125

Ser Arg Pro Gln Ile Thr Asn Glu Tyr Val Thr Arg Val Pro Ile Asp
        130                 135                 140

Tyr His Glu Ile Val Arg Ile Asp Arg Ser Gly Glu Cys Ser Ser Lys
145                 150                 155                 160

Ala Thr Tyr His Lys Asn Phe Met Phe Phe Glu Ala Tyr Asp Asn Asp
                165                 170                 175

Glu Arg Glu Lys Lys Leu Pro Leu Val Pro Ser Leu Leu Arg Ser Thr
                180                 185                 190

Val Ser Lys Ala Phe His Thr Thr Asn Phe Thr Lys Arg His Gln Thr
            195                 200                 205

Leu Gly Tyr Arg Thr Ser Thr Ser Val Asp Cys Val Val Glu Tyr Leu
        210                 215                 220

Gln Ala Arg Ser Val Tyr Pro Tyr Asp Tyr Phe Gly Met Ala Thr Gly
225                 230                 235                 240

Asp Thr Val Glu Ile Ser Pro Phe Tyr Thr Lys Asn Thr Thr Gly Pro
                245                 250                 255

Arg Arg His Ser Val Tyr Arg Asp Tyr Arg Phe Leu Glu Ile Ala Asn
                260                 265                 270

Tyr Gln Val Arg Asp Leu Glu Thr Gly Gln Ile Arg Pro Pro Lys Lys
            275                 280                 285

Arg Asn Phe Leu Thr Asp Glu Gln Phe Thr Ile Gly Trp Asp Ala Met
        290                 295                 300

Glu Glu Lys Glu Ser Val Cys Thr Leu Ser Lys Trp Ile Glu Val Pro
305                 310                 315                 320

Glu Ala Val Arg Val Ser Tyr Lys Asn Ser Tyr His Phe Ser Leu Lys
                325                 330                 335

Asp Met Thr Met Thr Phe Ser Ser Gly Lys Gln Pro Phe Asn Ile Ser
                340                 345                 350

Arg Leu His Leu Ala Glu Cys Val Pro Thr Ile Ala Ser Glu Ala Ile
            355                 360                 365

Asp Gly Ile Phe Ala Arg Lys Tyr Ser Ser Thr His Val Arg Ser Gly
        370                 375                 380

Asp Ile Glu Tyr Tyr Leu Gly Ser Gly Gly Phe Leu Ile Ala Phe Gln
385                 390                 395                 400

Lys Leu Met Ser His Gly Leu Ala Glu Met Tyr Leu Glu Glu Ala Gln
                405                 410                 415

Arg Gln Asn His Leu Pro Arg Gly Arg Glu Arg Gln
            420                 425
```

<210> SEQ ID NO 3
<211> LENGTH: 1287
<212> TYPE: DNA
<213> ORGANISM: Infectious laryngotracheitis virus

<400> SEQUENCE: 3

```
atggctagct tgaaaatgct gatctgcgtg tgcgtggcaa tcctgatccc atctacccta     60
tctcaagatt cacacggaat tgccggaata atagaccctc gtgatacagc cagcatggat    120
gttggaaaaa tctctttctc cgaagccatt gggtcggggg caccgaaaga accccagatt    180
agaaacagaa tttttgcgtg ctcatctcca actggcgcca gtgttgcgag gcttgcccag    240
ccacgacatt gtcaccgaca tgccgattcg actaacatga ctgaaggaat tgccgtagtc    300
ttcaagcaaa acattgcccc gtacgtcttt aatgtgactc tatactataa acatataacc    360
```

-continued

```
acagttacta cgtgggcatt attctcaaga ccccaaataa caaatgagta cgtgaccagg      420
gttccaatag actatcatga aattgtcagg attgatcgat cgggagaatg ctcatccaaa      480
gcaacgtatc ataaaattt catgttttt gaagcttacg acaatgatga acgagaaaaa       540
aaattgcccc tggttccatc actgttaaga tcaactgtct ccaaggcgtt tcatacaact      600
aactttacta agcgacatca aaccctggga taccgaacgt ctacatcggt cgactgtgtt      660
gtggaatatc tacaggctag atctgtatac ccgtatgatt actttggaat ggcgacaggt      720
gatacagtag aaatttctcc cttttatacc aaaaacacga ccggaccaag gcgtcacagt      780
gtctacagag actatagatt tctcgaaatc gcaaattatc aagtcaggga tttggaaacc      840
ggacaaataa gaccccctaa aaaagaaac tttctaacag atgaacaatt cactataggc       900
tgggatgcaa tggaagaaaa ggaatctgta tgtactctca gtaaatggat tgaagtcccg      960
gaagcagttc gtgtttcgta caaaaacagt taccactttt cacttaaaga tatgactatg     1020
acgttctcgt ccggaaaaca accttttaac atcagcaggc ttcatttggc tgaatgcgtt     1080
cctaccatag cttcggaggc catagatggc atctttgcca gaaagtatag ttcgactcat     1140
gtccgttctg gggacatcga atactatctc ggtagtggcg gatttctgat cgcatttcag     1200
aaactcatga gccatggctt ggctgaaatg tacctagaag aggcacaaag acaaaatcat     1260
ctcccgagag ggagagagcg tcgccaa                                         1287
```

<210> SEQ ID NO 4
<211> LENGTH: 40
<212> TYPE: PRT
<213> ORGANISM: Artificial
<220> FEATURE:
<223> OTHER INFORMATION: SV40 pA signal

<400> SEQUENCE: 4

Gly Asp Leu Tyr Lys Cys Gly Met Ala Asp Tyr Asp His Glu Gln Thr
1               5                   10                  15

Val Arg Thr Glu Gly Pro Glu Met Ser Leu Gly Thr Val Asn Arg Pro
            20                  25                  30

Ile Arg Pro Ile Tyr Ser Ser His
        35                  40

<210> SEQ ID NO 5
<211> LENGTH: 120
<212> TYPE: DNA
<213> ORGANISM: Artificial
<220> FEATURE:
<223> OTHER INFORMATION: SV40 pA signal

<400> SEQUENCE: 5

```
ggcgacctct acaaatgtgg tatggctgat tatgatcatg aacagactgt gaggactgag       60
gggcctgaaa tgagccttgg gactgtgaat cggccaataa ggcctattta ctcatcgcat      120
```

<210> SEQ ID NO 6
<211> LENGTH: 18
<212> TYPE: DNA
<213> ORGANISM: Artificial
<220> FEATURE:
<223> OTHER INFORMATION: Synthetic

<400> SEQUENCE: 6

```
tgtaaaacga cggccagt                                                    18
```

<210> SEQ ID NO 7
<211> LENGTH: 29
<212> TYPE: DNA
<213> ORGANISM: Artificial
<220> FEATURE:
<223> OTHER INFORMATION: Synthetic

<400> SEQUENCE: 7
ttcggtaccg gttattatta tttttgac                                29

<210> SEQ ID NO 8
<211> LENGTH: 30
<212> TYPE: DNA
<213> ORGANISM: Artificial
<220> FEATURE:
<223> OTHER INFORMATION: Synthetic

<400> SEQUENCE: 8
gggctgcaga gttattaata gtaatcaatt                              30

<210> SEQ ID NO 9
<211> LENGTH: 27
<212> TYPE: DNA
<213> ORGANISM: Artificial
<220> FEATURE:
<223> OTHER INFORMATION: Synthetic

<400> SEQUENCE: 9
gcactcggat ccattgacat ggctagc                                 27

<210> SEQ ID NO 10
<211> LENGTH: 30
<212> TYPE: DNA
<213> ORGANISM: Artificial
<220> FEATURE:
<223> OTHER INFORMATION: Synthetic

<400> SEQUENCE: 10
agatgccatc tatggcctcc gaagctatgg                              30

<210> SEQ ID NO 11
<211> LENGTH: 30
<212> TYPE: DNA
<213> ORGANISM: Artificial
<220> FEATURE:
<223> OTHER INFORMATION: Synthetic

<400> SEQUENCE: 11
tggctgaatg cgttcctacc atagcttcgg                              30

<210> SEQ ID NO 12
<211> LENGTH: 29
<212> TYPE: DNA
<213> ORGANISM: Artificial
<220> FEATURE:
<223> OTHER INFORMATION: Synthetic

<400> SEQUENCE: 12
cgggtacctt attcgtcttc gctttcttc                               29

<210> SEQ ID NO 13
<211> LENGTH: 30
<212> TYPE: DNA
<213> ORGANISM: Artificial
<220> FEATURE:
<223> OTHER INFORMATION: Synthetic

```
<400> SEQUENCE: 13
gccaggcgcg ccatttaccg tcattgacgt                                    30

<210> SEQ ID NO 14
<211> LENGTH: 30
<212> TYPE: DNA
<213> ORGANISM: Artificial
<220> FEATURE:
<223> OTHER INFORMATION: Synthetic

<400> SEQUENCE: 14
acgtcaatga cggtaaatgg cgcgcctggc                                    30

<210> SEQ ID NO 15
<211> LENGTH: 30
<212> TYPE: DNA
<213> ORGANISM: Artificial
<220> FEATURE:
<223> OTHER INFORMATION: Synthetic

<400> SEQUENCE: 15
cgtctagagg atctgacggt tcactaaacc                                    30

<210> SEQ ID NO 16
<211> LENGTH: 30
<212> TYPE: DNA
<213> ORGANISM: Artificial
<220> FEATURE:
<223> OTHER INFORMATION: Synthetic

<400> SEQUENCE: 16
ggctagatct gtatacccgt atgattactt                                    30

<210> SEQ ID NO 17
<211> LENGTH: 30
<212> TYPE: DNA
<213> ORGANISM: Artificial
<220> FEATURE:
<223> OTHER INFORMATION: Synthetic

<400> SEQUENCE: 17
cggtacctta ttgtctaaca aatgtatagt                                    30

<210> SEQ ID NO 18
<211> LENGTH: 30
<212> TYPE: DNA
<213> ORGANISM: Artificial
<220> FEATURE:
<223> OTHER INFORMATION: Synthetic

<400> SEQUENCE: 18
cggtacctta atctccacgt attacagtgt                                    30

<210> SEQ ID NO 19
<211> LENGTH: 30
<212> TYPE: DNA
<213> ORGANISM: Artificial
<220> FEATURE:
<223> OTHER INFORMATION: Synthetic

<400> SEQUENCE: 19
ttacatattt atctccacgt attacagtgt                                    30

<210> SEQ ID NO 20
<211> LENGTH: 30
```

```
<212> TYPE: DNA
<213> ORGANISM: Artificial
<220> FEATURE:
<223> OTHER INFORMATION: Synthetic

<400> SEQUENCE: 20
acgtggagat aaatatgtaa tgaacctgaa                                           30

<210> SEQ ID NO 21
<211> LENGTH: 30
<212> TYPE: DNA
<213> ORGANISM: Artificial
<220> FEATURE:
<223> OTHER INFORMATION: Synthetic

<400> SEQUENCE: 21
cggtacctta ttcgtcttcg ctttcttctg                                           30

<210> SEQ ID NO 22
<211> LENGTH: 1410
<212> TYPE: DNA
<213> ORGANISM: Recombinant herpes virus turkey

<400> SEQUENCE: 22
atggctagct tgaaaatgct gatctgcgtg tgcgtggcaa tcctgatccc atctacccta          60
tctcaagatt cacacggaat tgccggaata atagaccctc gtgatacagc cagcatggat         120
gttggaaaaa tctctttctc cgaagccatt gggtcggggg caccgaaaga accccagatt         180
agaaacagaa ttttttgcgtg ctcatctcca actggcgcca gtgttgcgag gcttgcccag        240
ccacgacatt gtcaccgaca tgccgattcg actaacatga ctgaaggaat tgccgtagtc         300
ttcaagcaaa acattgcccc gtacgtcttt aatgtgactc tatactataa acatataacc         360
acagttacta cgtgggcatt attctcaaga ccccaaataa caaatgagta cgtgaccagg         420
gttccaatag actatcatga aattgtcagg attgatcgat cgggagaatg ctcatccaaa         480
gcaacgtatc ataaaaattt catgtttttt gaagcttacg acaatgatga acgagaaaaa         540
aaattgcccc tggttccatc actgttaaga tcaactgtct ccaaggcgtt tcatacaact         600
aactttacta agcgacatca aaccctggga taccgaacgt ctacatcggt cgactgtgtt         660
gtggaatatc tacaggctag atctgtatac ccgtatgatt actttggaat ggcgacaggt         720
gatacagtag aaatttctcc cttttatacc aaaaacacga ccggaccaag gcgtcacagt         780
gtctacagag actatagatt tctcgaaatc gcaaattatc aagtcaggga tttggaaacc         840
ggacaaataa gaccccctaa aaaagaaac tttctaacag atgaacaatt cactataggc         900
tgggatgcaa tggaagaaaa ggaatctgta tgtactctca gtaaatggat tgaagtcccg         960
gaagcagttc gtgtttcgta caaaaacagt taccactttt cacttaaaga tatgactatg        1020
acgttctcgt ccggaaaaca acctttttaac atcagcaggc ttcatttggc tgaatgcgtt        1080
cctaccatag cttcggaggc catagatggc atctttgcca gaaagtatag ttcgactcat        1140
gtccgttctg gggacatcga atactatctc ggtagtggcg gatttctgat cgcatttcag        1200
aaactcatga gccatggctt ggctgaaatg tacctagaag aggcacaaag acaaaatcat        1260
ctcccgagag ggagagagcg tcgccaaggc gacctctaca aatgtggtat ggctgattat        1320
gatcatgaac agactgtgag gactgagggg cctgaaatga gccttgggac tgtgaatcgg        1380
ccaataaggc ctatttactc atcgcattag                                         1410

<210> SEQ ID NO 23
```

-continued

```
<211> LENGTH: 30
<212> TYPE: DNA
<213> ORGANISM: Artificial
<220> FEATURE:
<223> OTHER INFORMATION: Synthetic

<400> SEQUENCE: 23
cggtacctta ttggcgacgc tctctccctc                                  30

<210> SEQ ID NO 24
<211> LENGTH: 24
<212> TYPE: DNA
<213> ORGANISM: Artificial
<220> FEATURE:
<223> OTHER INFORMATION: Synthetic

<400> SEQUENCE: 24
ggggaagtct tccggttaag ggac                                        24

<210> SEQ ID NO 25
<211> LENGTH: 30
<212> TYPE: DNA
<213> ORGANISM: Artificial
<220> FEATURE:
<223> OTHER INFORMATION: Synthetic

<400> SEQUENCE: 25
cataccacat ttgtagaggt cctattggcg                                  30

<210> SEQ ID NO 26
<211> LENGTH: 30
<212> TYPE: DNA
<213> ORGANISM: Artificial
<220> FEATURE:
<223> OTHER INFORMATION: Synthetic

<400> SEQUENCE: 26
cgagagggag agagcgtcgc caataggacc                                  30

<210> SEQ ID NO 27
<211> LENGTH: 24
<212> TYPE: DNA
<213> ORGANISM: Artificial
<220> FEATURE:
<223> OTHER INFORMATION: Synthetic

<400> SEQUENCE: 27
tagcggcacg gaaacagata gaga                                        24
```